United States Patent
Wickham et al.

(10) Patent No.: US 11,419,652 B2
(45) Date of Patent: Aug. 23, 2022

(54) THREAD FORM FOR BONE SCREW

(71) Applicant: WARSAW ORTHOPEDIC, INC., Warsaw, IN (US)

(72) Inventors: Jeffrey Wickham, Ooltewah, TN (US); Mark Dace, Collierville, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 538 days.

(21) Appl. No.: 16/395,409

(22) Filed: Apr. 26, 2019

(65) Prior Publication Data

US 2020/0337752 A1 Oct. 29, 2020

(51) Int. Cl.
*A61B 17/86* (2006.01)

(52) U.S. Cl.
CPC ...... *A61B 17/8625* (2013.01); *A61B 17/8605* (2013.01)

(58) Field of Classification Search
CPC ............ A61B 17/8605; A61B 17/8615; A61B 17/8625; A61B 17/863; A61B 17/7035
See application file for complete search history.

(56) References Cited

U.S. PATENT DOCUMENTS

| | | | | |
|---|---|---|---|---|
| 5,334,204 A | * | 8/1994 | Clewett | A61B 17/8625 606/312 |
| 6,152,666 A | * | 11/2000 | Walther | F16B 25/0015 411/311 |
| 8,828,060 B2 | * | 9/2014 | Biedermann | A61B 17/7049 606/270 |
| 9,707,013 B2 | | 7/2017 | Rezach et al. | |
| 9,872,711 B2 | | 1/2018 | Hynes et al. | |
| 9,883,948 B2 | | 2/2018 | Chavarria et al. | |
| 9,943,340 B2 | * | 4/2018 | Whipple | A61B 17/8615 |
| 9,949,776 B2 | | 4/2018 | Mobasser et al. | |
| 9,962,171 B2 | | 5/2018 | Rezach et al. | |
| 9,974,569 B2 | | 5/2018 | Lehmann, Jr. et al. | |
| 9,993,270 B2 | | 6/2018 | Butler | |
| 10,028,770 B2 | | 7/2018 | Rezach et al. | |
| 10,123,825 B2 | * | 11/2018 | Whipple | A61B 17/864 |
| 10,172,650 B2 | | 1/2019 | Hynes et al. | |
| 10,335,215 B2 | * | 7/2019 | Biedermann | A61B 17/869 |
| 2006/0241596 A1 | | 10/2006 | Rezach | |
| 2007/0233138 A1 | | 10/2007 | Figueroa et al. | |

(Continued)

FOREIGN PATENT DOCUMENTS

JP 2004-512899 4/2004

OTHER PUBLICATIONS

International Search Report and Written Opinion dated Feb. 11, 2020 from corresponding International Application No. PCT/US2019/057576.

(Continued)

*Primary Examiner* — Anu Ramana

(57) ABSTRACT

A bone screw including a head portion, a neck portion, and a shaft portion is provided. The shaft portion includes a first end, an opposite second end, a helical thread form, and a shank. The first end of the shaft portion is attached to the neck portion, and the helical thread form extends around the shank between the first end and the second end. The thread form terminates at a thread-termination surface adjacent the first end of the shaft portion, where the thread-termination surface affords an abrupt transition into the shank.

20 Claims, 9 Drawing Sheets

(56) References Cited

U.S. PATENT DOCUMENTS

| | | |
|---|---|---|
| 2012/0065691 A1 | 3/2012 | Simonson |
| 2012/0328394 A1* | 12/2012 | Biedermann ........... F16B 43/02 |
| | | 411/436 |
| 2015/0105830 A1* | 4/2015 | Biedermann ...... A61B 17/8605 |
| | | 606/317 |
| 2016/0242820 A1* | 8/2016 | Whipple ............ A61B 17/8695 |
| 2017/0245898 A1 | 8/2017 | May et al. |

OTHER PUBLICATIONS

U.S. Appl. No. 15/843,938, filed Dec. 15, 2017 in the name of May et al.
U.S. Appl. No. 16/287,700, filed Feb. 27, 2019 in the name of Rezach et al.
U.S. Appl. No. 16/380,739, filed Apr. 10, 2019 in the name of Rezach et al.
U.S. Appl. No. 16/386,328, filed Apr. 17, 2019 in the name of Rezach et al.
U.S. Appl. No. 16/395,319, filed Apr. 26, 2019 in the name of Wickham et al.

* cited by examiner

THREAD FORM FOR BONE SCREW

FIELD

The present technology is generally related to a thread form for a bone screw.

BACKGROUND

Conventional thread forms used on conventional bone screws typically include angled faces to facilitate thread termination. These angled faces are provided on the thread forms adjacent trailing ends of the conventional bone screws. The closer the angled faces approaches to 90° to the central axes of the conventional bone screws, the more turns of the thread forms are possible. However, there is at least one significant tradeoff to modifying the angled faces in such a manner. As the angled faces approach 90° to the central axis, the thinner the angled faces are as they get closer to neck portions of the bone screw, and the thinner the thread forms are as the thread forms spiral down toward the neck portions from the angled faces. Thus, there is a need for a thread form that limits portions of thread forms from being disadvantageously thin, while also serving in maximizing the turns of the thread forms.

SUMMARY

The techniques of this disclosure generally relate to thread forms for a bone screw incorporating a thread-termination surface.

In one aspect, the present disclosure provides a bone screw including a trailing end, an opposite leading end, and a central axis extending through the trailing end and the leading end; a head portion extending from the trailing end toward the leading end; a neck portion attached to the head portion and extending from the head portion toward to the leading end; and a shaft portion attached to the neck portion and extending from the neck portion to the leading end, the shaft portion including a first end, an opposite second end, a helical thread form, and a shank, the first end being attached to the neck portion, the second end being collocated with the leading end, and the helical thread form extending around the shank between the first end and the second end; and where the thread form terminates at a thread-termination surface adjacent the first end of the shaft portion, where the thread-termination surface affords an abrupt transition into the shank over less than a half turn of the shaft portion.

In another aspect, the disclosure provides a bone screw including a trailing end, an opposite leading end, and a central axis extending through the trailing end and the leading end; a head portion extending from the trailing end toward the leading end; a neck portion attached to the head portion and extending from the head portion toward to the leading end; and a shaft portion attached to the neck portion and extending from the neck portion to the leading end, the shaft portion including a first end, an opposite second end, a helical thread form, and a shank, the first end being attached to the neck portion, the second end being collocated with the leading end, and the helical thread form extending around the shank between the first end and the second end, the helical thread being continuous about the shank and having a variable height relative to the central axis in a direction perpendicular to the central axis; where the thread form terminates at a thread-termination surface adjacent the first end of the shaft portion, where the thread-termination surface affords an abrupt transition into the shank over less than a half turn of the shaft portion.

In yet another aspect, the disclosure provides a bone screw including a trailing end, an opposite leading end, and a central axis extending through the trailing end and the leading end; a head portion extending from the trailing end toward the leading end; a neck portion attached to the head portion and extending from the head portion toward to the leading end; and a shaft portion attached to the neck portion and extending from the neck portion to the leading end, the shaft portion including a first end, an opposite second end, a helical thread form, and a shank, the first end being attached to the neck portion, the second end being collocated with the leading end, and the helical thread form extending around the shank between the first end and the second end, the helical thread being continuous about the shank and having a variable height relative to the central axis in a direction perpendicular to the central axis; where the thread form terminates at a thread-termination surface adjacent the first end of the shaft portion, where the thread-termination surface affords an abrupt transition into the shank over less than a half turn of the shaft portion, and where the thread form includes a face facing the head portion and at least a portion of the face is oriented at approximately 90° to the central axis of the bone screw.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
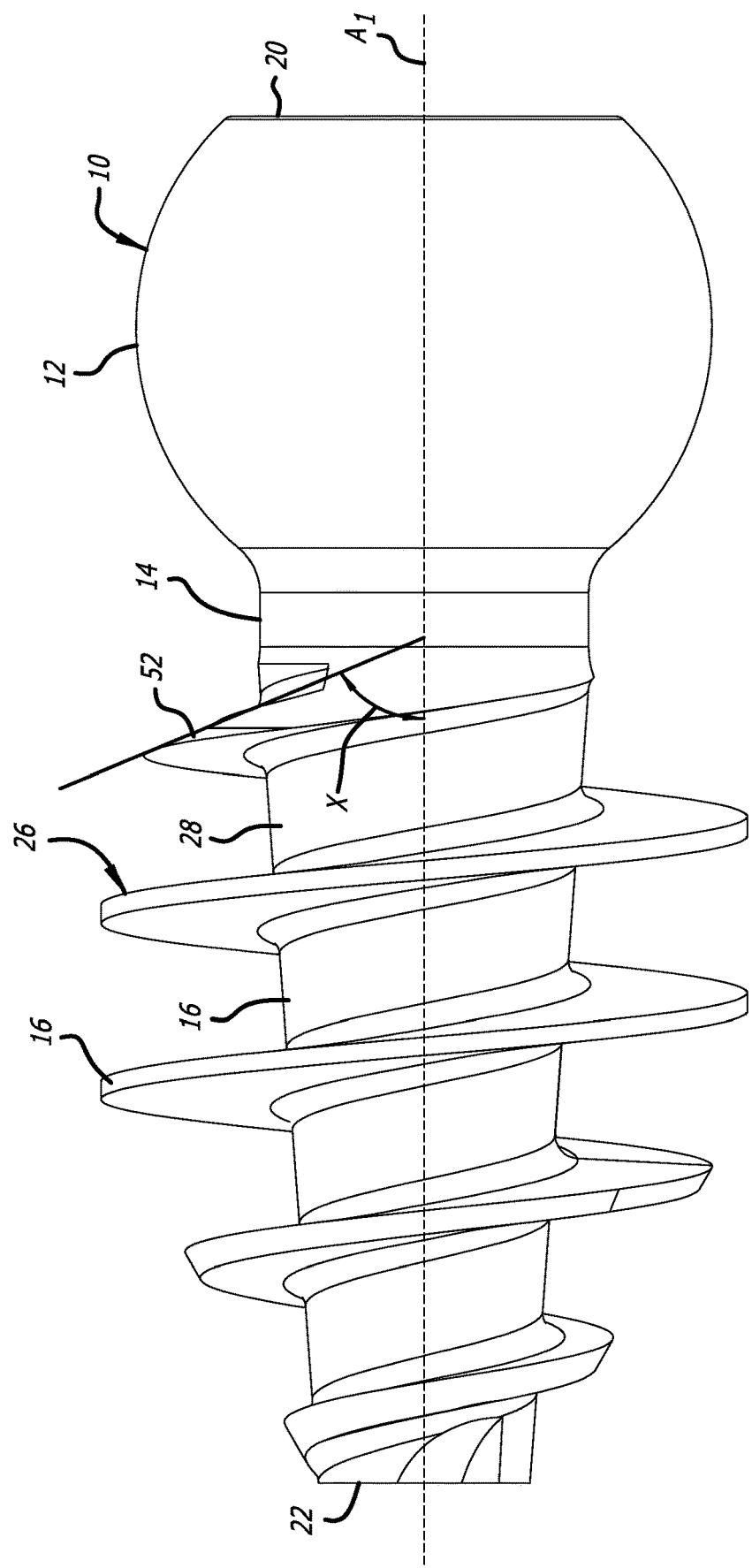
FIG. 1 is a side, elevational view that illustrates a prior art bone screw.
Figure 7:
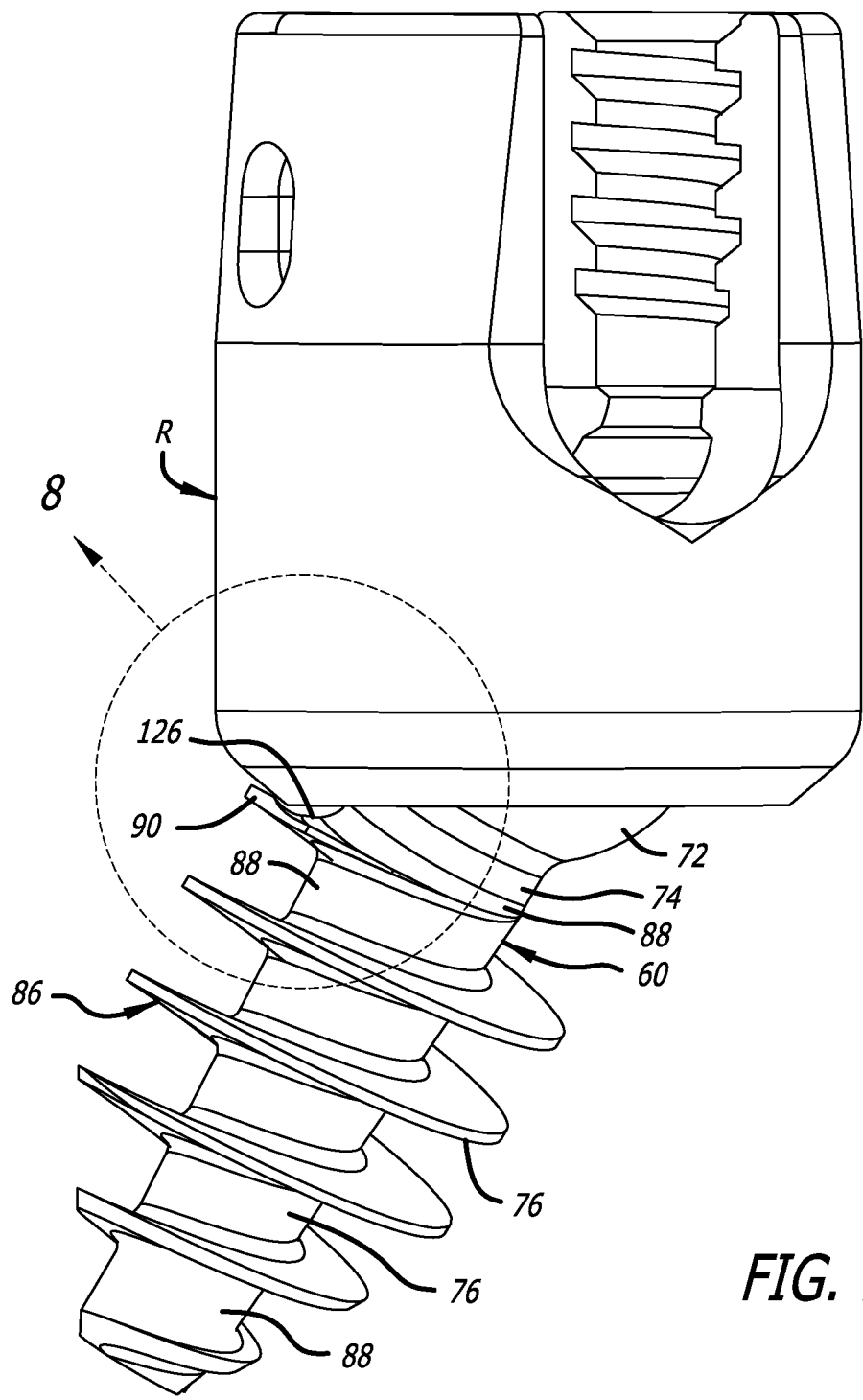
FIG. 7 is a side, elevational view of a receiver received on the bone screw of FIG. 6.
Figure 8:
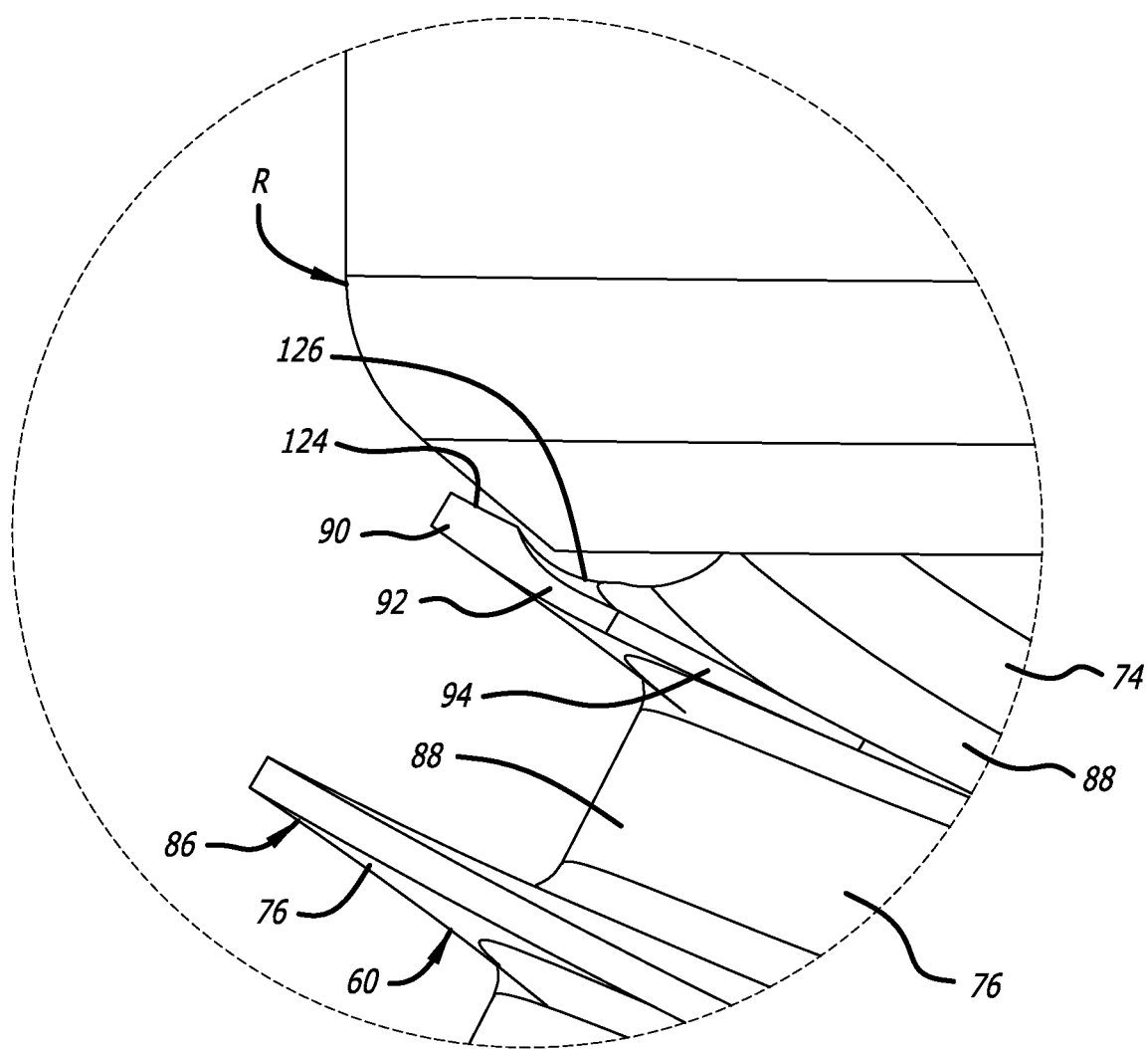
FIG. 8 is an enlarged, side, elevational view of FIG. 7.
Figure 9:
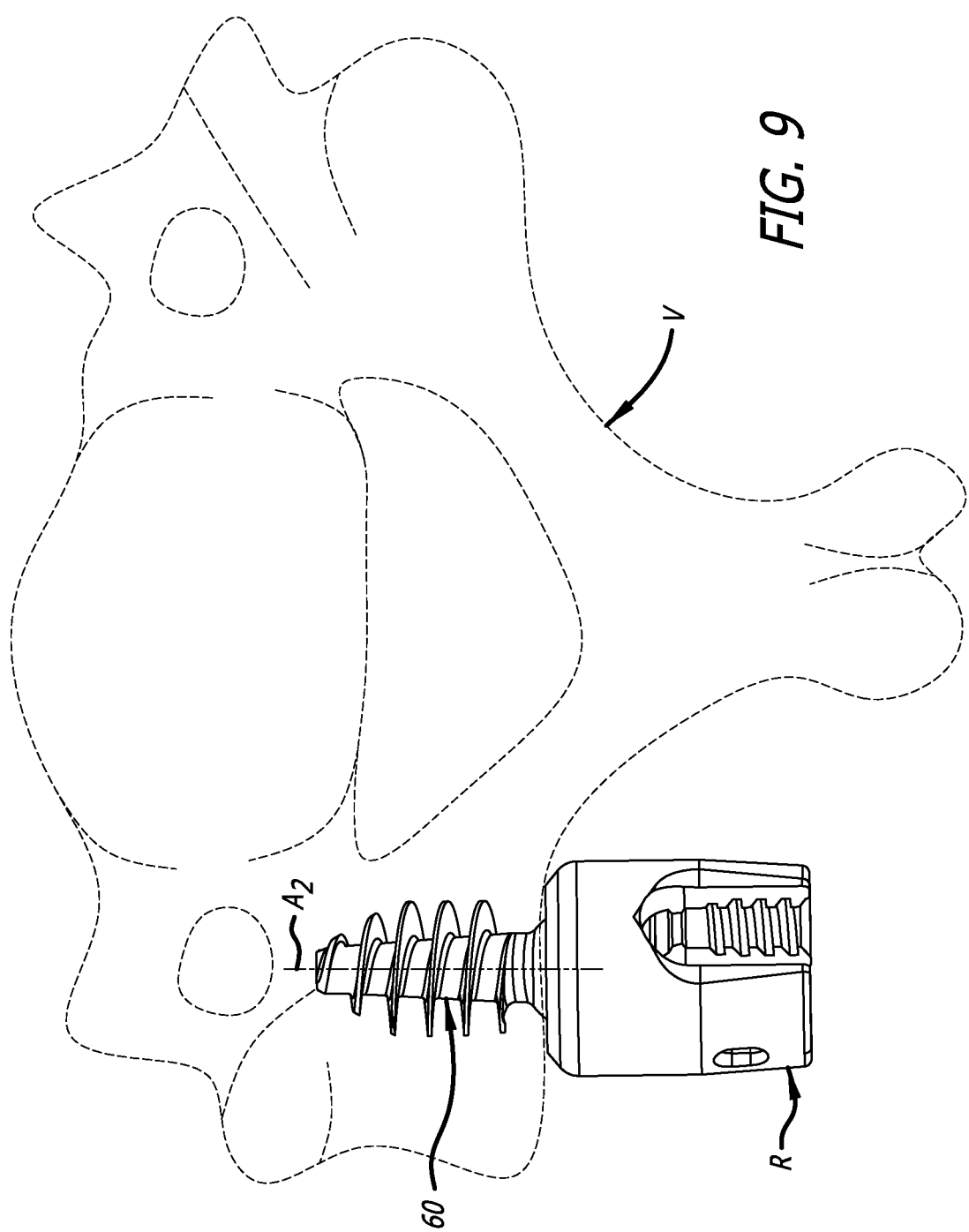
FIG. 9 is top plan view of the bone screw and the receiver of FIG. 7 positioned with respect to a vertebrae of a patient.

A prior art bone screw 10 that can be used as a cervical lateral mass screw is depicted in FIG. 1. The bone screw 10 is used to penetrate tissue such as, for example, bone, and can be used in association with a receiver R (FIGS. 7-9). The receiver R can be, for example, a receiver disclosed in U.S. Ser. No. 15/843,938, which is herein incorporated by reference in its entirety.

The bone screw 10, as depicted in FIG. 1, includes a head portion 12, a neck portion 14, a shaft portion 16, and a central axis $A_1$. Furthermore, the receiver R is received on the head portion 12, and is capable of pivotal and rotational movement relative to the head portion 12. The bone screw 10 includes a trailing end 20 and a leading end 22, and the central axis $A_1$ extends through the trailing end 20 and the leading end 22. The head portion 12 extends from the trailing end 20 to the neck portion 14, the neck portion 14 extends from the head portion 12 to the shaft portion 16, and the shaft portion 16 extends from the neck portion 14 to the leading end 22. The head portion 12 includes a tool-engaging depression (not shown), and the shaft portion 16 includes a helical thread form 26 and a shank 28. The thread form 26 is formed around the shank 28, the thread form 26 at one end terminates adjacent the neck portion 14 and at the other end terminates adjacent the leading end 22, and the axis of the thread form 26 corresponds to the central axis $A_1$ of the bone screw 10. The thread form 26 facilitates penetration of the bone screw 10 into the tissue such as bone.

Figure 2:
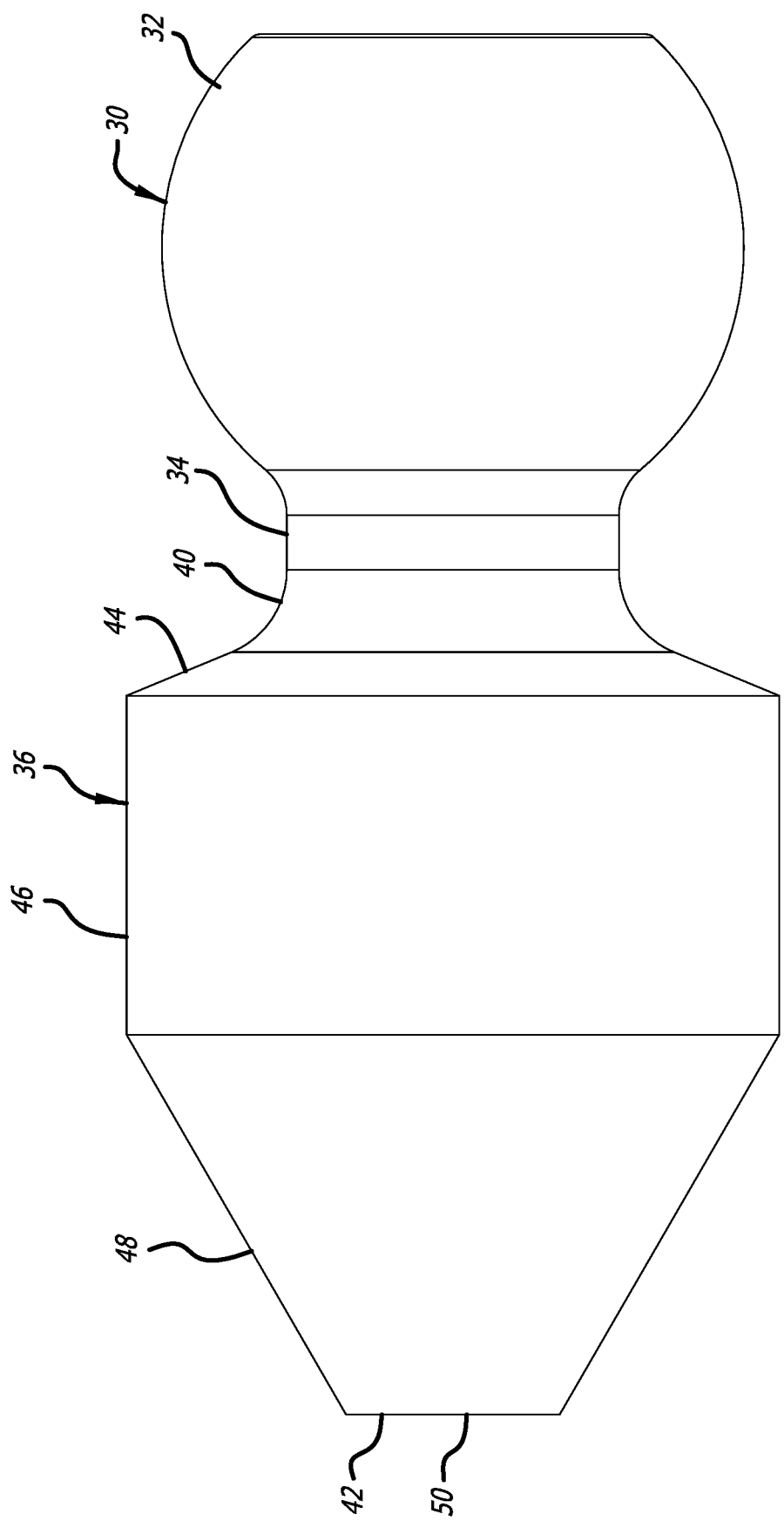
FIG. 2 is a side, elevational view that illustrates a blank used to form the prior art bone screw of FIG. 1.

The bone screw 10 is formed from a blank 30 depicted in FIG. 2. The blank 30 includes a head portion 32, a neck portion 34, and a body portion 36. The head portion 32 corresponds to the head portion 12, the neck portion 34 corresponds to the neck portion 14, and the thread form 26 and the shank 28 are fabricated from the body portion 36.

The body portion 36 includes a first end 40 adjacent the neck portion 34, and a second end 42 corresponding to the leading end 22 of the bone screw 10. Furthermore, the body portion 36 includes a first portion 44, a second portion 46, and a third portion 48. The first portion 44 extends from the neck portion 34 to the second portion 46, the second portion 46 extends from the first portion 44 to the third portion 48, and the third portion 48 extends from the second portion 46 to the second end 42. As depicted in FIG. 2, the first portion 44 is generally frusto-conical, the second portion 46 is cylindrical, and the third portion 48 is frusto-conical. Furthermore, as depicted in FIG. 2, the first portion 44 smoothly transitions into the neck portion 34, the first portion 44 sharply transitions into the second portion 46, the second portion 46 sharply transitions into the third portion 48, and the third portion 48 terminates at an end surface 50 of the third portion 48.

The thread form 26 is formed from a fabrication process applied to the body portion 36, and the thread form 26 extends between the first end 40 and the second end 42 of what was the body portion 36. As depicted in FIG. 2, the thread form 26 is continuous about the shank 28, and has a constant pitch and a variable major diameter in a direction perpendicular to the central axis $A_1$. Conventional thread forms, like the thread form 26, typically include angled faces such as, for example, an angled face 52 adjacent the endpoint of the thread form 26. The angled face 52 is formed by a portion of the generally frusto-conical shape of the first portion 44. Furthermore, the shapes of the first portion 44, the second portion 46, and the third portion 48 also ultimately affect the variable major diameter of the thread form 26 fabricated from the body portion 36. In the direction from the trailing end to the leading end in FIG. 2, first portion 44 includes an increasing diameter relative to the central axis $A_1$, the second portion 46 includes a constant diameter relative to the central axis $A_1$, and the third portion 48 includes a decreasing diameter relative to the central axis $A_1$.

Thus, when looking from the opposite direction, i.e., in the direction from the leading end to the trailing end in FIG. 1, the variable major diameter of thread form 26 relative to the central axis $A_1$ increases along what was the third portion 48, is generally constant along what was the second portion 46, and decreases along what was the first portion 44. Because of the shape of the first portion 44, the thread form 26 decreases in diameter from what was the second portion 46 until it ends adjacent the neck portion 34. Furthermore, as depicted in FIG. 1, the angled face 52 causes the thread form 26 to get thinner adjacent the neck portion 34, and the thinning of the thread form 26 continues from angled face 52 as the thread form 26 transitions into the shank 28 by spiraling down toward the neck portion 34. The thinning of the thread form 26 can be disadvantageous, and occurs over more than one turn of the thread form 26 as it transitions into the shank 28 adjacent the neck portion 34.

As depicted in FIG. 2, the angled face 52 (formed from a portion the first portion 44) is at an angle X of approximately 67° to the central axis $A_1$. The closer the portion of the first portion 44 forming the angled face 52 approaches 90° to the central axis $A_1$, the more turns of the thread form 26 are possible. However, there is at least one significant tradeoff to modifying the portion of the first portion 44 forming the angled face 52 to be closer to 90° to the central axis $A_1$. As the portion of the first portion 44 forming the angled face 52 approaches 90° to the central axis $A_1$, the thinner the angled face 52 becomes as it spiral inwards and gets closer to the neck portion 14, and the thinner the thread form 26 gets as it spirals down toward the neck portion 34 from the angled face 52.

Figure 4:
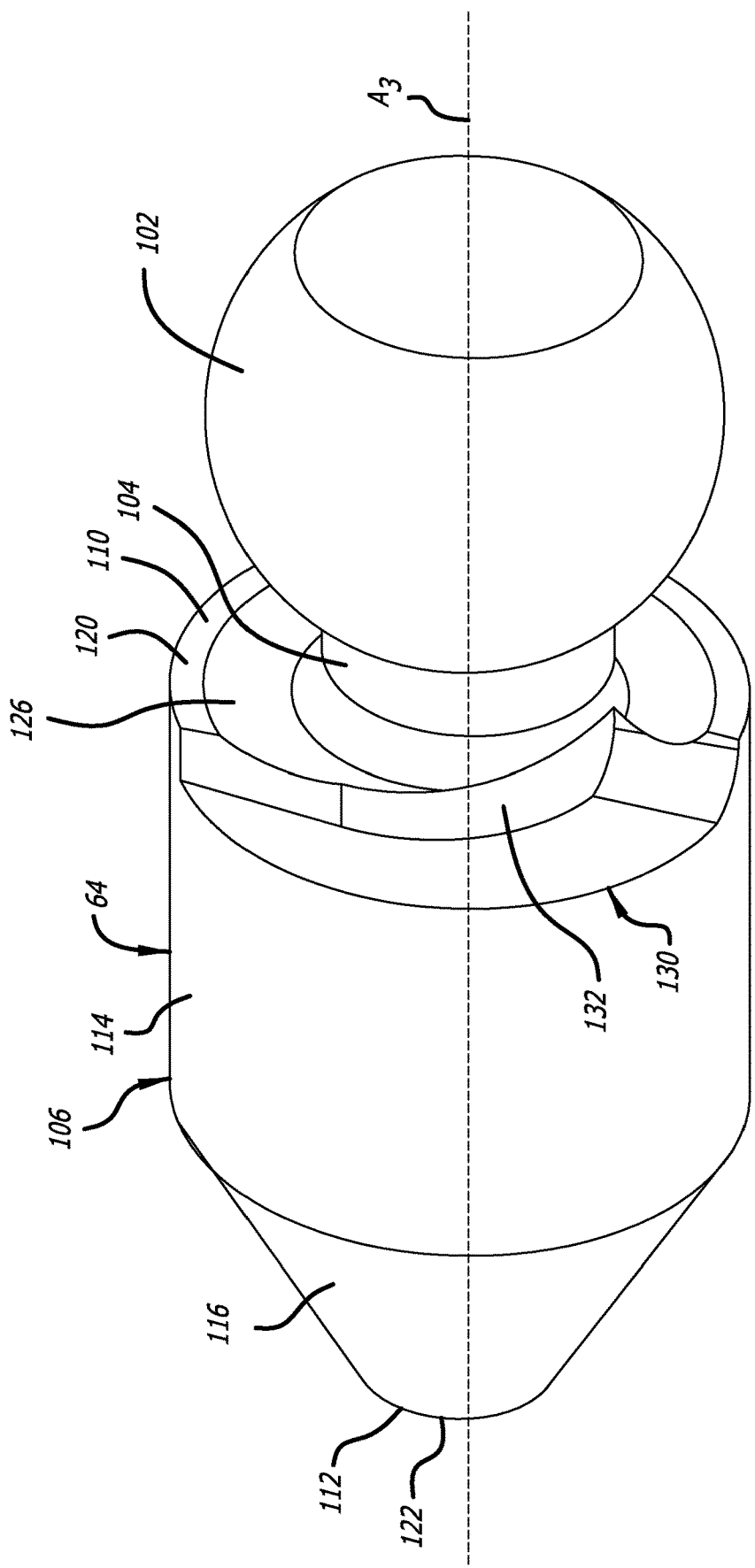
FIG. 4 is a side, perspective view that illustrates a modified blank used in fabricating an embodiment of the bone screw.
Figure 5:
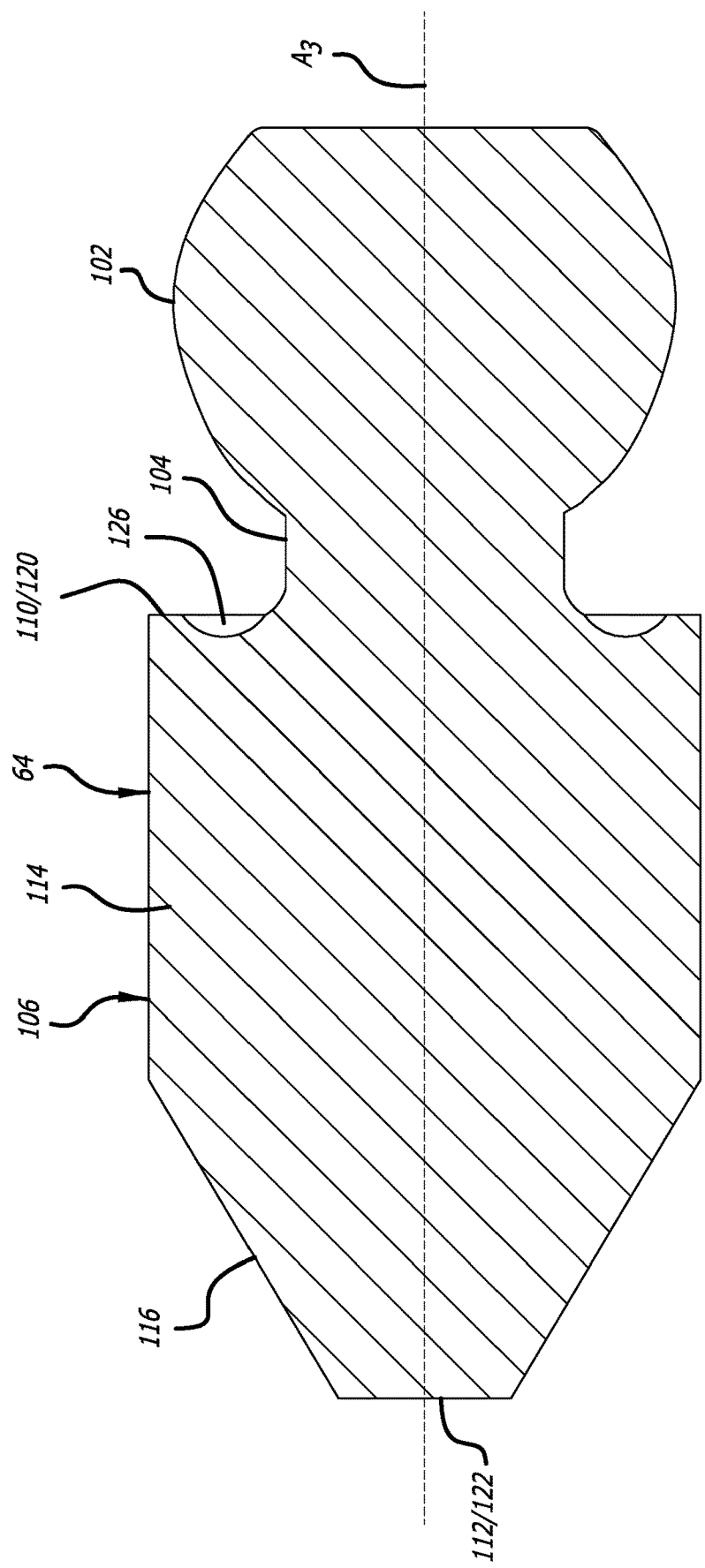
FIG. 5 is a side, cross-sectional view of the modified blank of FIG. 4.

A bone screw according to an embodiment of the present disclosure is generally indicated by the numeral 60 in FIGS. 6-9. A fabrication process can be applied to a blank 62 (FIG. 3) to form a modified blank 64 (FIGS. 4 and 5), and the bone screw 60 can be fabricated from the modified blank 64. The bone screw 60 can, but is not limited, to being used as a cervical lateral mass screw. The configuration of the bone screw 60 and the modified blank 64 used to form the bone screw 60 are used in limiting the disadvantageously thin portions of the turns of the thread form 26 discussed in association with the bone screw 10.

The bone screw 60 can be used to penetrate tissue such as, for example, bone, and can be used in association with a receiver R (FIGS. 7-9). The bone screw 60 includes a head portion 72, a neck portion 74, a shaft portion 76, and a central axis $A_2$. Furthermore, the receiver R is received on the head portion 72 (FIGS. 7-9), and is capable of pivotal and rotational movement relative to the head portion 72. The bone screw 60 includes a trailing end 80 and a leading end 82, and the central axis $A_2$ extends through the trailing end 80 and the leading end 82. The head portion 72 extends from the trailing end 80 to the neck portion 74, the neck portion 74 extends from the head portion 72 to the shaft portion 76, and the shaft portion 76 extends from the neck portion 74 to the leading end 82. The head portion 72 includes a tool-engaging depression 84, and the shaft portion 76 includes a helical thread form 86 and a shank 88. The thread form 86 is formed around the shank 88, the thread form 86 at one end terminates adjacent the neck portion 74 and at the other end terminates adjacent the leading end 82, and the axis of the thread form 86 corresponds to the central axis $A_2$ of the bone screw 60. The thread form 86 facilitates penetration of the bone screw 60 into the tissue such as bone.

Unlike the bone screw 10, the bone screw 60 limits disadvantageous thinning of the thread form 26 associated with the bone screw 10 while serving in maximizing the turns of the thread form 86. The thread form 86 abruptly terminates at a thread-termination surface 90 along the shaft portion 76 instead of, like the thread portion 26, transitioning into the shank 28 by spiraling down toward the neck portion 34.

Figure 6:
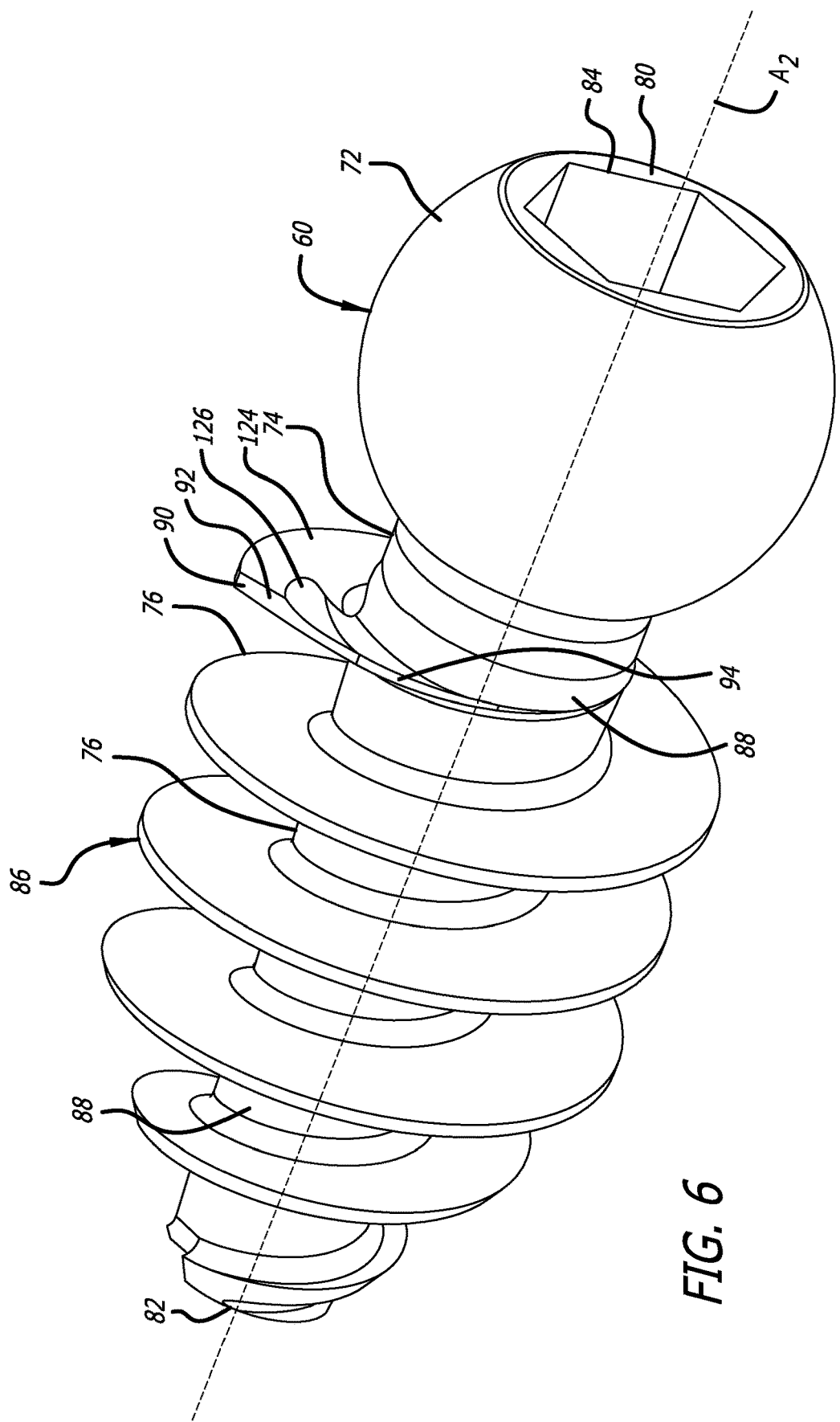
FIG. 6 is a side, perspective view that illustrates an embodiment of the bone fabricated using the blank of FIG. 3. and the modified blank of FIG. 4.

The thread termination surface 90 is formed from a truncation of the thread form 86 that limits the disadvantageous thinning of the thread form 86. The thread-termination surface 90 does not follow a helix defined by the thread form 86, and the thread-termination surface 90 can include flattened surface(s) and curved surface(s) that limit the disadvantageous thinning of the thread form 86. As depicted in FIGS. 6-8, the thread-termination surface 90 includes a first surface portion 92 that can be substantially flattened and a second surface portion 94 that can be substantially curved. The first surface portion 92 includes a thickness that substantially corresponds to the thicknesses of the other turns of the thread form 86, and the second surface portion 94 abruptly transitions into the shank 88 adjacent the neck portion 74. Unlike the angled face 52 of the thread form 26, the thread-termination surface affords the abrupt transition of the thread-termination surface 90 into the shank 88 to occur over less than a half turn of the shaft portion 76. The abrupt transition afforded by the second surface portion 94 of the thread-termination surface 90 limits portions of the turns of the thread form 86 from being disadvantageously thin, while serving in maximizing the turns of the thread form 86. And the maximization of the turns of the thread form 86 allows the thread form 86 to terminate closer to the head portion 72.

As discussed above, a fabrication process can be applied to the blank 62 (FIG. 3) to form the modified blank 64 (FIGS. 4 and 5), and the bone screw 60 can be fabricated from the modified blank 64. The blank 62 includes a head portion 102, a neck portion 104, a body portion 106, and a central axis $A_3$. The head portion 102 corresponds to the head portion 72, the neck portion 104 corresponds to the neck portion 74, and the thread form 86 and the shank 88 are fabricated from the body portion 106.

Figure 3:
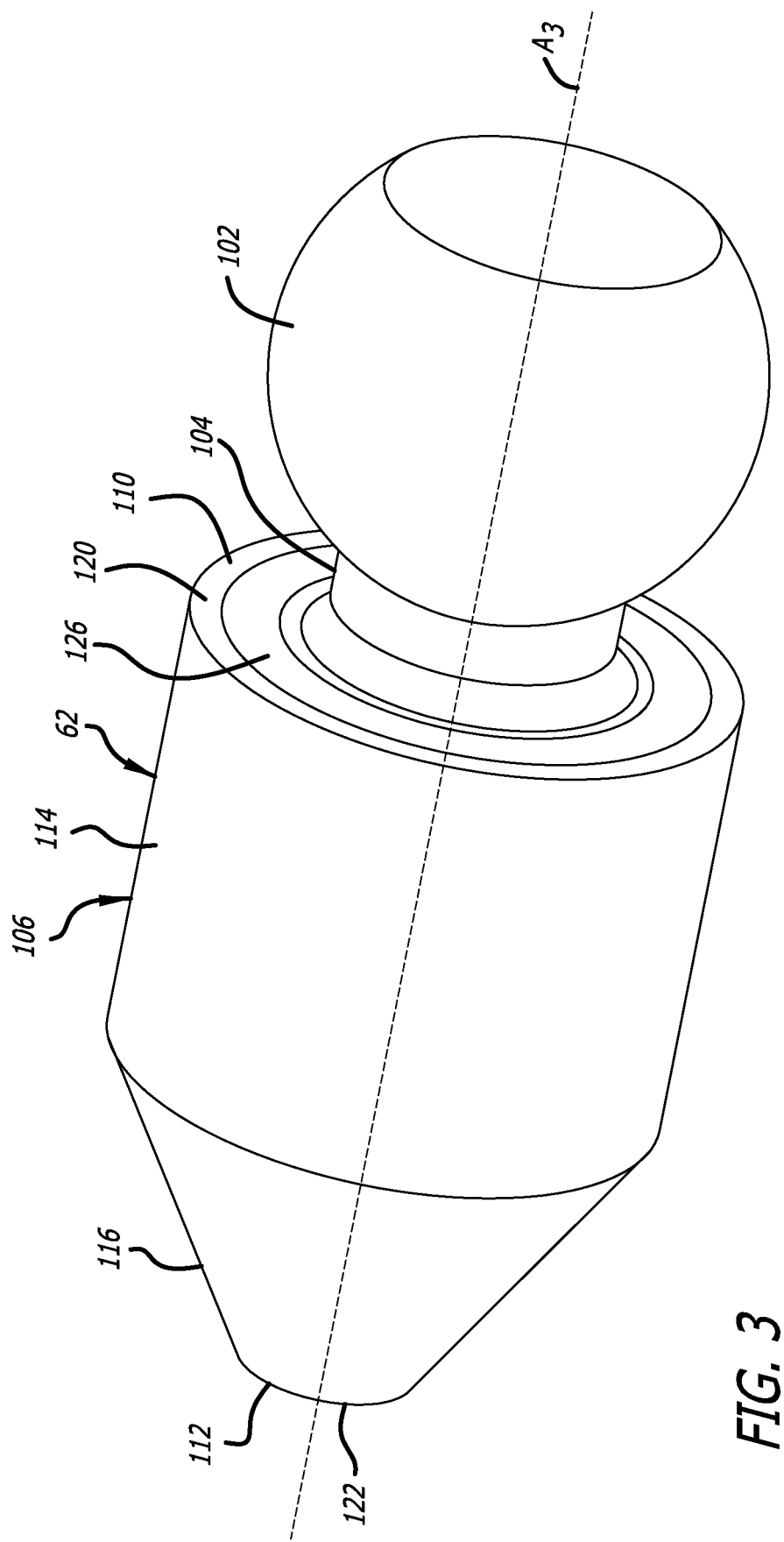
FIG. 3 is a side, perspective view that illustrate a blank used in fabricating an embodiment of a bone screw.

The body portion 106 includes a first end 110 adjacent the neck portion 104, and a second end 112 corresponding to the leading end 82 of the bone screw 60. Furthermore, the body portion 106 includes a first portion 114 and a second portion 116. The first portion 114 extends from the neck portion 104 to the second portion 116, and the second portion 116 extends from the first portion 114 to the second end 112. As depicted in FIG. 3, the first portion 114 can be generally cylindrical, and the second portion 116 can be generally frusto-conical. Furthermore, as depicted in FIG. 3, an end surface 120 of the first portion 114 smoothly transitions into the neck portion 104, the first portion 114 sharply transitions into the second portion 116, and the second portion 116 terminates at an end surface 122 of the second portion 116. The end surface 120 can be oriented at 90° or approximately 90° relative to the central axis $A_3$, and a portion of the end surface 120 remains after formation of the thread form 86 that forms a face 124 facing the head portion 72 (FIG. 6). Additionally, a relief cut 126 is formed in the end surface 120, and a portion of the relief cut 126 remains after formation of the thread portion 86 (FIGS. 6-8) to increase the ability of the receiver R to pivot (FIGS. 7 and 8) relative to the head portion 72.

The modified blank 64 can be formed from a fabrication process applied to the blank 62. Like the blank 62, the modified blank 64 includes the head portion 102, the neck portion 104, the body portion 106, and the central axis $A_3$. To form the modified blank 64, a portion of the body portion 106 of the blank 62 can be removed during the fabrication process to form a cavity 130. For example, a cutting and/or a grinding process can be used to remove material from the blank 62 to form the cavity 130 of the blank 64. The cavity 130 includes a surface 132, and the first surface portion 92 and the second surface portion 94 of the thread-termination surface 90 are formed from the surface 132.

The thread form 86 and the thread-termination surface 90 can be formed from a fabrication process applied to the body portion 106, and the thread form 86 extends between the first end 110 and the second end 112 of what was the body portion 106. As depicted in FIG. 6, the thread form 86 is continuous about the shank 88, and has a constant pitch and a variable major diameter in a direction perpendicular to the central axis $A_2$.

As discussed above, the thread form 86 terminates at the thread-termination surface 90. Furthermore, the shapes of the first portion 114 and the second portion 116 also ultimately affect the variable major diameter of the thread form 86 fabricated from the body portion 106. In the direction from the trailing end to the leading end in in FIG. 5, first portion 114 can include a constant diameter, and the second portion 116 can include a decreasing diameter. Thus, when looking from the opposite direction in FIG. 6, i.e., in the direction from the leading end to the trailing end, the variable major diameter of the thread form 86 increases along what was the second portion 116, is generally constant along what was the first portion 114, and terminates at the thread-termination surface 90. As such, the thread form 86 includes a first major diameter relative to the central axis $A_2$ adjacent what was the first end 110 of the body portion 106, a second major diameter relative to the central axis $A_2$ between what was the first end 110 and the second end 112 of the body portion 106, and at least one third major diameter relative to the central axis $A_2$ adjacent was the second end 112 of the body portion 106. The first, second, and third major diameters are measured in direction perpendicular and relative to the central axis $A_2$, and the first and second major diameters can be substantially equal to one another, the first and second major diameters can be each greater than the at least one third major diameter, and the thread-termination surface 90 can extend inwardly to the shank 88 from the first major diameter.

As discussed above, the abrupt transition afforded by the second surface portion 94 of the thread-termination surface 90 limits portions of the turns of the thread form 86 being disadvantageously thin, and serves in maximizing the turns of the thread form 86. Maximizing the turns of the thread form 86 allows more turns over the length of the shaft portion 76, and the configuration of the thread form 86 increases pullout force by approximately 5% to the thread form 26. As such, the length of the shaft portion 76 (of the bone screw 70) can be shorter than the shaft portion 16 (of the bone screw 10), while having the same pullout strength.

The receiver R, as depicted in FIGS. 7-9, can be received on the head portion 72, and the bone screw 60, as depicted in FIG. 9, can be driven into bone such as, for example, a vertebra V. As depicted in FIG. 9, the bone screw 70 is used as a cervical lateral mass screw, and the maximization of the turns of the thread form 86 using the thread-termination surface 90 increases the pullout strength of the bone screw 70 in comparison to conventional prior art bone screws such as the bone screw 10 used in a similar fashion.

Multiples of the combination of the bone screw 60 and the receiver R can be similarly positioned along a spinal column, and instrumentation such as, for example, surgical rods (not shown) can be attached to the receivers R of adjacent ones of the combinations of the bone screw 60 and the receiver R to facilitate correction of spinal abnormalities. The pivotal and rotational movement of the receiver R relative to the head portion 72 allows the receiver R to be adjusted to accommodate placement of a surgical rod. Furthermore, the degree of capable pivotal movement can be increased by use of the relief cut 126. As depicted in FIGS. 7 and 8, the relief cut 126 allows the receiver R to pivot into space that would have been occupied by the thread form 86 to correspondingly increase the degree of capable pivotal movement of the receiver R relative to the head portion 102.

It should be understood that various aspects disclosed herein may be combined in different combinations than the combinations specifically presented in the description and the accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A unitary bone screw comprising:
    a trailing end, an opposite leading end, and a central axis extending through the trailing end and the leading end;
    a head portion extending from the trailing end toward the leading end;
    a neck portion attached to the head portion and extending from the head portion toward to the leading end; and
    a shaft portion attached to the neck portion and extending from the neck portion to the leading end, the shaft portion including a first end, an opposite second end, a helical thread form, and a shank, the first end being attached to the neck portion, the second end being collocated with the leading end, and the helical thread form extending around the shank between the first end and the second end;
    wherein the helical thread form includes a first crest and a thread-termination surface, wherein the helical thread form terminates at the thread-termination surface, wherein the first crest and the thread-termination surface are located adjacent the first end of the shaft portion, wherein the thread-termination surface includes a flattened first surface portion that extends inwardly toward the shank from adjacent a maximum diameter of the first crest, wherein the flattened first surface portion resides in a first plane parallel to the central axis and spaced apart from the shank, and includes a maximum height measured in a direction parallel to the central axis in the first plane, and wherein the thread-termination surface affords an abrupt transition into the shank over less than a half turn of the shaft portion.

2. The bone screw of claim 1, wherein the first crest of the helical thread form has a first major diameter in a direction perpendicular to the central axis.

3. The bone screw of claim 2, wherein the thread-termination surface includes a second surface portion in addition to the flattened first surface portion, the flattened first surface portion extending from the first crest to the second surface portion, and the second surface portion transitioning into the shank.

4. The bone screw of claim 3, wherein the second surface portion includes a curved surface portion.

5. The bone screw of claim 2, wherein the thread form includes a face facing the head portion, and the face includes a relief cut adjacent the thread-termination surface.

6. The bone screw of claim 2, wherein the thread form includes a face facing the head portion, and at least a portion of the face is oriented at approximately 90° to the central axis of the bone screw.

7. The bone screw of claim 6, wherein the thread form includes a third crest with a third major diameter in a direction perpendicular to the central axis, the third crest being positioned adjacent the second end of the shaft portion, the first major diameter and the second major diameter each being greater than the third major diameter.

8. The bone screw of claim 2, wherein the thread form includes a second crest with a second major diameter in a direction perpendicular to the central axis, the second crest being positioned between the first end and the second end of the shaft portion, and the first major diameter of the first crest being substantially equal to the second major diameter of the second crest.

9. The bone screw of claim 1, wherein the head portion includes a tool-engaging depression, and the bone screw is insertable into bone via rotational force applied thereto via the tool-engaging depression.

10. A unitary bone screw comprising:
    a trailing end, an opposite leading end, and a central axis extending through the trailing end and the leading end;
    a head portion extending from the trailing end toward the leading end;
    a neck portion attached to the head portion and extending from the head portion toward to the leading end; and
    a shaft portion attached to the neck portion and extending from the neck portion to the leading end, the shaft portion including a first end, an opposite second end, a helical thread form, and a shank, the first end being attached to the neck portion, the second end being collocated with the leading end, and the helical thread form extending around the shank between the first end and the second end, the helical thread being continuous about the shank and having a variable height relative to the central axis in a direction perpendicular to the central axis;
    wherein the helical thread form includes a first crest and a thread termination surface, wherein the helical thread form terminates at the thread-termination surface, wherein the first crest and the thread-termination surface are located adjacent the first end of the shaft portion, wherein the thread-termination surface includes a flattened first surface portion that extends inwardly toward the shank from adjacent a maximum diameter of the first crest, wherein the flattened first surface portion resides in a first plane parallel to the central axis and spaced apart from the shank, and includes a maximum height measured in a direction parallel to the central axis in the first plane, and wherein the thread-termination surface affords an abrupt transition into the shank over less than a half turn of the shaft portion.

11. The bone screw of claim 10, wherein the first crest of the helical thread has a first major diameter in a direction perpendicular to the central axis.

12. The bone screw of claim 11, wherein the thread-termination surface includes a second surface portion in addition to the flattened first surface portion, the flattened first surface portion extending from the first crest to the second surface portion, and the second surface portion transitioning into the shank.

13. The bone screw of claim 12, wherein the second surface portion includes a curved surface portion.

14. The bone screw of claim 11, wherein the thread form includes a face facing the head portion, and the face includes a relief cut adjacent the thread-termination surface.

15. The bone screw of claim 11, wherein the thread form includes a face facing the head portion, and at least a portion of the face is oriented at approximately 90° to the central axis of the bone screw.

16. The bone screw of claim 15, wherein the thread form includes a third crest with a third major diameter relative to the central axis in a direction perpendicular to the central axis, the third crest being positioned adjacent the second end of the shaft portion, the first major diameter and the second major diameter each being greater than the third major diameter.

17. The bone screw of claim 11, wherein the thread form includes a second crest with a second major diameter relative to the central axis in a direction perpendicular to the central axis, the second crest being positioned between the first end and the second end of the shaft portion, and the first major diameter of the first crest being substantially equal to the second major diameter of the second crest.

18. The bone screw of claim 10, wherein the head portion includes a tool-engaging depression, and the bone screw is insertable into bone via rotational force applied thereto via the tool-engaging depression.

19. A unitary bone screw comprising:
a trailing end, an opposite leading end, and a central axis extending through the trailing end and the leading end;
a head portion extending from the trailing end toward the leading end;
a neck portion attached to the head portion and extending from the head portion toward to the leading end; and
a shaft portion attached to the neck portion and extending from the neck portion to the leading end, the shaft portion including a first end, an opposite second end, a helical thread form, and a shank, the first end being attached to the neck portion, the second end being collocated with the leading end, and the helical thread form extending around the shank between the first end and the second end, the helical thread being continuous about the shank and having a variable height relative to the central axis in a direction perpendicular to the central axis;
wherein the helical thread form includes a first crest and a thread-termination surface, wherein the helical thread form terminates at the thread-termination surface, wherein the first crest and the thread-termination surface are located adjacent the first end of the shaft portion, wherein the thread-termination surface includes a flattened first surface portion that extends inwardly toward the shank from adjacent a maximum diameter of the first crest, wherein the flattened first surface portion resides in a first plane parallel to the central axis and spaced apart from the shank, and includes a maximum height measured in a direction parallel to the central axis in the first plane, wherein the thread-termination surface affords an abrupt transition into the shank over less than a half turn of the shaft portion, and wherein the thread form includes a face facing the head portion and at least a portion of the face is oriented at approximately 90° to the central axis of the bone screw.

20. The bone screw of claim 19, wherein the thread-termination surface includes a substantially curved second surface portion in addition to the flattened first surface portion, the flattened first surface portion extending from the first crest with a first major diameter of the thread form to the second surface portion, and the second surface portion transitioning into the shank.

* * * * *